United States Patent
Coelingh Bennink

(10) Patent No.: US 6,642,219 B1
(45) Date of Patent: Nov. 4, 2003

(54) PROGESTOGEN-ANTIPROGESTOGEN REGIMENS

(75) Inventor: Herman Jan Tijmen Coelingh Bennink, Driebergen (NL)

(73) Assignee: Akzo Nobel N.V., Arnhem (NL)

(*) Notice: Subject to any disclaimer, the term of this patent is extended or adjusted under 35 U.S.C. 154(b) by 0 days.

(21) Appl. No.: 09/554,429
(22) PCT Filed: Nov. 11, 1998
(86) PCT No.: PCT/EP98/07221
§ 371 (c)(1), (2), (4) Date: Jun. 26, 2000
(87) PCT Pub. No.: WO99/25360
PCT Pub. Date: May 27, 1999

(30) Foreign Application Priority Data

Nov. 14, 1997 (EP) .............................................. 97203543
May 8, 1998 (EP) .............................................. 98201464

(51) Int. Cl.⁷ .............................................. A61K 31/56
(52) U.S. Cl. ........................ 514/177; 514/178; 514/170; 514/171; 514/169
(58) Field of Search ................................ 514/177, 178, 514/169, 170, 171

(56) References Cited

U.S. PATENT DOCUMENTS

| | | | |
|---|---|---|---|
| 4,576,609 A | 3/1986 | Hageman et al. .............. 8/103 |
| 4,847,089 A | 7/1989 | Kramer et al. .............. 424/405 |
| 5,292,878 A | 3/1994 | Hamersma et al. | |
| 5,521,166 A | 5/1996 | Grubb | |

FOREIGN PATENT DOCUMENTS

| | | | |
|---|---|---|---|
| DE | 37 29 442 A1 | 3/1989 | ............ D06L/3/00 |
| DE | 43 30 234 A | 3/1995 | |
| DE | 43 44 463 A | 6/1995 | |
| DE | 44 26 601 A1 | 2/1996 | |
| DE | 195 31 936 A | 2/1997 | |
| GB | 2 217 204 A | 4/1989 | ............ A61L/2/12 |
| HU | 208 487 B | 9/1990 | |
| RU | 94007635 A1 | 10/1995 | |
| WO | WO 92/20228 | 11/1992 | ........... A01N/59/24 |
| WO | WO 93/17686 | 9/1993 | |
| WO | WO 93/18798 | 9/1993 | ............ A61L/2/12 |
| WO | WO 93 21927 | 11/1993 | |
| WO | WO 94 04156 | 3/1994 | |
| WO | WO 96 15794 | 5/1996 | |
| WO | WO 97/49407 | 12/1997 | |
| WO | WO 98/03622 | 1/1998 | ............ C11D/3/39 |
| WO | WO 98/03623 | 1/1998 | ............ C11D/3/39 |
| WO | WO 88/07370 | 10/1998 | |

OTHER PUBLICATIONS

Wagner B.L. et al., "16Alpha–substituted Analogs of the Antiprogestin RU486 Induce A Unique Conformation in the Human Progesterone Receptor REsulting in Mixed Agonist Activity," Proceedings of the National Academy of Sciences of USA, vol. 93, No. 16, Aug. 6, 1996, pp. 8739–8744.

Chwalisz Kristof et al., "The Use of Progesterone Antagonists for CervicalRipening and as an Adjunct to Labour and Delivery," Human Reproduction, 1994, vol. 9, No. 1, pp. 131–161, (abstract only).

Kekkonen et al., "Sequential Regimen of the Antiprogesterone RU486 and Synthetic Progestin for Contraception," Fertility and Sterility, vol. 60, No. 4, 1993, pp. 610–615.

Danielsson et al., Improving cycle control in progestogen–only contraceptive pill users by intermittent treatment with a new anti–progestogen, Human Reproduction, 2002, pp. 2588–2593, vol. 17, No. 10.

Spitz et al., The Use of Progesterone Antagonists and Progesterone Receptor Modulators in Contraception, 2000, pp. 817–823, Steroids, vol. 65.

van Heusden et al., Single monthly administration of the anti–progestagen Org 31710 in users of the 75 µg desogestrel progestagen–only pill: effects on pituitary–ovarian activity, Human Reproduction, 2000, pp. 629–636, vol. 5, No. 3.

Primary Examiner—Russell Travers
Assistant Examiner—S. Jiang
(74) Attorney, Agent, or Firm—TraskBritt

(57) ABSTRACT

An estrogen-free contraceptive is provided which does not have the bleeding-related drawbacks of conventional progestogen-only pills. Thus the invention is a contraceptive kit comprising a combined means for the simultaneous daily administration of a progestogen as the sole contraceptively effective ingredient and an anti-progestogen. Said combined means preferably is in the form of tablets having a normal contraceptive dose of the progestogen and low dose of the anti-progestogen.

5 Claims, No Drawings

PROGESTOGEN-ANTIPROGESTOGEN REGIMENS

CROSS-REFERENCE TO RELATED APPLICATIONS

This application is 371 of PCT/EP98/07221, filed Nov. 10, 1998, designating the United States of America, corresponding to PCT International Publication WO 99/25360 (published in English on May 27, 1999).

The invention relates to a contraceptive kit (drug delivery system) comprising means (a) for the daily administration of a progestogen and means (b) for the administration of an anti-progestogen, providing a contraceptive regimen of the estrogen-free, i.e. progestogen-only type.

It has been known for some time that contraception can be achieved by the oral administration of sufficient quantities of a progestogen to a female of child-bearing age. Contraceptive preparations that minimise the incidence of menstrual spotting, break through bleeding, variations in menstrual cycle length and amenorrhea are preferred. It is further preferred to use contraceptive regimens that minimise the amounts of estrogens and progestogens used. Preparations that fulfil many of these requirements are disclosed in WO 93/21927, wherein a contraceptive regimen free from estrogens is described, the active, ovulation-inhibiting ingredient being a progestational agent. This agent is combined, particularly intermittently, with an anti-progestogen in a dosage amount equivalent to 10 mg to 250 mg of RU 486 per dose. The regimen used is a regimen wherein only levonorgestrel is administered as the progestogen, except that on days 1, 30, 60, 90, 120, 150, and 180 a dosage of the anti-progestogen RU 486 is administered. In fact the regimen is a progestogen-only regimen, interrupted by anti-progestogen administration at the beginning of each cycle. Although this regimen is a considerable improvement over existing regimens comprising estrogens, the bleeding profile is still not perfect since it recurs slowly after an almost bleeding-free interval, and further improvement is therefore desirable.

"Progestogen-only pills" are a preferred method of contraception for breast-feeding mothers, older women, women for whom estrogen is contraindicated, women who are hypertensive, and women who develop migraine headaches when taking a combined pill (i.e. one containing an estrogen and progestogen component). See, e.g. "Contraception for women over the age of 35", *IPPF Medical Bulletin*, 22: 3–4 (1988) and P. W. Howie "The progestogen-only pill", *Brit. J. Obstet. Gynaecol.*, 92: 1001–2 (1985).

While different progestogen-only regimens have been described, they are associated with incomplete ovulation inhibition, and relatively high failure rates. Vessey et al "Progestogen-only oral contraception. Findings in a large prospective study with special reference to effectiveness", *Brit. J. Family Planning*, 292: 526–30 (1986). It has been suggested to increase the daily dosage of progestogen in order to induce complete ovulation inhibition, however such an increase in dosage also increases the frequency of intermenstrual bleeding (i.e. "spotting"), which is clearly not desired. E. Diczfalusy et al, *Progestogens in Therapy*, p. 150 (Raven Press, N.Y. 1983). Moreover, a high prevalence of functional ovarian cysts have been reported with progestogen only contraceptive regimens, which resolve after discontinuation of the progestogen-only contraceptive. Fotherby, K. "The Progestogen-pill", in: Filshie et al eds. *Contraception: Science and Practice*, pp. 94–108 (1989), and Howie, supra.

A need exists for a progestogen-only contraceptive regimen which more effectively inhibits ovulation, while still not increasing the frequency of intermenstrual bleeding, or leading to persistent functional ovarian cysts. The solution to this need by adding intermittently an anti-progestogen needs further elaboration.

Surprisingly a contraceptive regimen satisfying the above need has now been found in that a progestogen is administered at a dose sufficient to inhibit ovulation and an anti-progestogen is administered at a dose not affecting ovulation, but sufficient to retain good cycle control and almost completely decreasing the amount of spotting and bleeding, i.e. in general a dose sufficient to prevent irregular bleeding and which leads to an improved, more predictable and more acceptable, bleeding pattern as compared to a progestogen-only regimen with or without intermittent anti-progestogen administration.

The invention thus resides in a contraceptive kit of the type mentioned in the opening paragraph, wherein said means (a) and (b) are designed to constitute a combined means (c) for the simultaneous daily administration of the progestogen and the anti-progestogen, the daily dosage amount of the anti-progestogen being below the lower boundary indicated in WO 93/21927, i.e. below the equivalent of 10 mg of RU 486.

The invention also includes a pharmaceutical product (i.e. the dosage units or the package containing the dosage units), a method of using the product, and a process of manufacturing the pharmaceutical product. The invention also includes a method of providing contraception involving administering to a woman the above-mentioned regimens.

Progestogens for use with the invention are 3-keto-desogestrel (etonogestrel), desogestrel, gestodene, levonorgestrel, norgestrel and other progestogens commonly used for contraception. Desogestrel has the chemical name 13-ethyl-11-methylene-18,19-di-nor-17α-pregn-4en-20-yn-17-ol, and is the preferred progestogen. Desogestrel is believed to be metabolised in the body into 3-ketodesogestrel (etonogestrel). Preferably the dosage units contain 75 μg of desogestrel or 3-ketodesogestrel, or an amount of other progestogens having an effect equivalent with that of 75 μg of desogestrel. Based on practically applied doses, levonorgestrel, desogestrel, and 3-keto-desogestrel are relatively equipotent in progestogenic activity. Gestodene is approximately 1.5 times as potent as these compounds. Norgestrel is about one-half as potent as levonorgestrel. Highly suitable are also progestogens of a newer generation, a preferred example of which is Org 30659, known from EP 210 678, the IUPAC name of which is (17α)-17-hydroxy-11-methylene-19-norpregna-4,15-dien-20-yn-3-one.

The anti-progestogen can be an inhibitor of progesterone synthesis, such as epostane, azastene or trilostane (Creange, Contraception 24, 289, 1981; Drugs of the Future 7, 661, 1982, van der Spuy et al., Contraception 35, 111, 1987; U.S. Pat. No. 3,296,255) or a progesterone receptor antagonist, or any such pharmaceutically suitable agent that counteracts the normal biological activity of progesterone, such as antibodies or ligands bindable to progestogens or to the progesterone receptor.

A suitable anti-progestogen is a progesterone receptor antagonist. Such compounds are widely known, e,g from EP 277 676, EP 289 073, EP 549 041, EP 582,338, and numerous other publications. Good examples are RU 486 (IUPAC name: (11β,17β)-11-[4-(demethylamino)-phenyl]-17-hydroxy-17-(1-propynyl)esta-4,9diene-3-one), Onapristone, Org 31710[(6α,11β,17β)-11-(4-dimethylaminophenyl)-6-methyl-4',5'-dihydrospiro-[estra- 4,9-diene-17,2'-(3'H)-furan]-3-one], and Org 33628[(11β, 17α)-11-(4-acetylphenyl)-17,23-epoxy-19,24-dinorchola-4,9,20-trien-3-one], which are all particularly suited in the practice of the present invention.

The main requirement for the daily dose of anti-progestogen is that it is sufficient to prevent irregular bleeding. Preferably, said dose is as low as possible. Thus, the daily dose of anti-progestogen is generally chosen so as to be equivalent to a daily dose of the reference anti-progestogen RU 486 of from 0.05 to 5 mg, and preferably of from 0.1 mg to 2 mg. For most anti-progestogens this will mean the daily administration of the corresponding fixed dose. Thus in the case of Org 33628 and Org 31710, which are somewhat more potent anti-progestogens, the daily dosage amount will typically be in the range of from 0.02 to 4 mg, and preferably of from 0.05 to 2 mg. The average skilled person will appreciate that in some cases it is preferred to adapt the dosage regimen so as to have an exposure to the anti-progestogen which is equivalent with the above daily dose of reference. This can be routinely determined on the basis of the half-life of a given compound. Thus, e.g., Org 33628 and RU 486 (having respective half-lives of approximately 15 hours and 20 hours) when administered daily in the above-indicated low dose will lead to a corresponding daily exposure of anti-progestogen, while Org 31710 (having a half-life of 50 hours) when administered daily will not effectively lead to daily exposure of a low dose, but to a cumulation of the anti-progestogen level. In order to attain the beneficial effects of the continuous low-dose regimen described above, Org 31710 can be administered every two days, typical dosage amounts ranging from 0.05–5 mg.

The combined means (c) may comprise any number of daily tablets containing the progestogen and the anti-progestogen. Contrary to the known "progestogen only" or "estrogen free" contraceptives, the package of daily tablets is free from tablets containing solely a progestogen: essentially, all tablets comprise a combination of progestogen and anti-progestogen. For practical reasons, it is preferred to provide a kit having at least 28 daily dosage units, as this is the normal length of the menstrual cycle. It is also possible for both the progestogen and the anti-progestogen to be incorporated into a controlled release device such as an implant or a vaginal ring. It may also be incorporated into an IUD (intra uterine device). In principle, the combined means (c) for administering the progestogen and the anti-progestogen may contain two different forms of administration. It is preferred, however, for both substances to be contained in the same dosage units for oral administration, which then form said combined means (c). In any event, said combined means may also comprise (alone, or combined with either or both of the progestogen and the anti-progestogen) a single active substance having the required mixed profile of progestogenic and anti-progestogenic properties. Such compounds are known, see, e.g., Sobek et al. in ENDO'97, page 549 (Poster Sessions of the Endocrine Society, No. P3-452) and Wagner et al. in Proc.Natl.Acad.Sci.USA, Vol.93, pp8739–8744 (1996).

The term "dosage unit" generally refers to physically discrete units suitable as unitary dosages for humans, each containing a predetermined quantity of active material calculated to produce the desired effect, for instance tablets, pills, powders, suppositories, capsules and the like.

Methods and compositions for making such dosage units are well-known to those skilled in the art. For example, conventional techniques for making tablets and pills, containing active ingredients, are described in the standard reference, Gennaro et al., Remington's Pharmaceutical Sciences, (18th ed., Mack Publishing Company, 1990, see especially Part 8: Pharmaceutical Preparations and Their Manufacture).

For making dosage units, e.g. tablets, the use of conventional additives, e.g. fillers, colorants, polymeric binders and the like is contemplated. In general any pharmaceutically acceptable additive which does not interfere with the function of the active compounds can be used in the one or more of the compositions.

Suitable carriers with which the compositions can be administered include lactose, starch, cellulose derivatives and the like used in suitable amounts. Lactose is a preferred carrier. Mixtures of carriers can also be used.

A process of manufacturing the kit of the invention comprises mixing predetermined quantities of progestogen (for instance desogestrel, 3-ketodesogestrel, or mixtures thereof) and anti-progestogen (for instance Org 31710) with predetermined quantities of excipients and converting the mixture into dosage units containing progestogen and anti-progestogen. Preferred kits contain a total of at least 28 of said daily sequential dosage units.

Converting the mixture into dosage units generally involves moulding the mixture into a tablet, filling a capsule with a dried mixture, or filling a capsule with a wet mixture.

A preferred process of manufacturing the pharmaceutical product according to the invention involves incorporating the desired dosages of contraceptive steroid (for example desogestrel, 3-ketodesogestrel, or mixtures thereof) into tablets by techniques such as wet granulation tableting techniques. The package containing the dosage units will generally contain between 28 and 364 (13 times 28) dosage units.

As to kits containing sequential daily dosage units for oral administration, it should be stressed that the contraceptive kit of the present invention is markedly different from and, in fact, a considerable improvement over, the known contraceptive kits of the "progestogen-only" type, also those in which, besides a progestogen, an anti-progestogen is administered as well (i.e. more correctly described as an "estrogen-free" regimen). The known contraceptive regimens of this type comprise a multiphasic combination of sequential daily dosage units containing solely the progestogen, as well as sequential daily dosage units containing a progestogen and an anti-progestogen. Now, contrary to these known regimens, the present invention is characterised in that the regimen does not contain any dosage units having only the progestogen, i.e. the sequential daily dosage units form a continuous, monophasic combination of the progestogen and the anti-progestogen. This leads to the considerable advantage, that a much lower amount of anti-progestogen per dosage unit can be administered, while an improved cycle-control is obtained.

As indicated above, the kit according to the invention may also comprise any of the active substances in a form other than that of a daily tablet. It is possible for one, e.g. the progestogen, to be in the form of a daily tablet and the other in the form of a sustained-release device, such as an implant, an intra-uterine device, or an intravaginal article, such as a vaginal ring, or vice versa. Just as with daily tablets, also in the case of other dosage forms, it is preferred if the combined means (c) according to the invention is actually one means, i.e. both the progestogen and the anti-progestogen are released from the same sustained-release device. Notably the very fact that the contraceptive regimen of the present invention is a continuous, monophasic regimen, makes it even better possible, from a technical point of view, to provide other methods of administration.

Methods of making sustained-release devices such as implants and vaginal rings are known in the art. In this respect, reference is made to Jorge Heller *Drug Delivery in the Plastics Age*, in "Innovations in Drug Delivery", Tom Sam and Jasper Fokkens ed., pages 134–145. For a preferred contraceptive implant, EP 303 306 is referred to. Many designs of a vaginal ring releasing two substances are known to the person skilled in the art. The preferably ring-shaped drug delivery system that can be used in the present invention comprises at least one compartment comprising a thermoplastic polymer core containing at least the progestogen and the anti-progestogen in a ratio by weight that allows a direct release from the said polymer of both compounds in physiologically required amounts. To this end the progestogen is initially dissolved in the core polymer in a relatively low degree of supersaturation, preferably being 1 to about 6 times of the amount by weight necessary for obtaining the saturation concentration of said progestogen in said core polymer at 25° C., and the anti-progestogen is initially dissolved in the core polymer in a concentration being lower than that of the said progestogenic compound, and a thermoplastic skin (outer layer) being permeable for the progestogen and the anti-progestogen.

The invention also pertains to a method of treatment. This refers to the administration of the anti-progestogen to women who, as a result of using a conventional progestogen-only regimen, suffer from extensive and/or irregular bleeding. In that respect, the invention is a method of treatment of bleeding induced by a progestogen-only contraceptive regimen, wherein an anti-progestogen is administered daily at a dose, calculated as RU 486 equivalent, of from 0.05 mg to 5 mg, and preferably of from 0.1 to 2 mg, so as to obtain a better controlled, and more predictable bleeding pattern.

In conjunction with the above, the invention also pertains to a novel medical indication of the daily administration of an anti-progestogen. Thus, the invention also resides in the use of an anti-progestogen for manufacturing a medicament for the treatment (by daily administration of a dose equivalent to a dose of RU 486 of from 0.05 mg to 5 mg) of bleeding resulting from the use of a progestogen-only contraceptive.

The invention is hereinafter illustrated with reference to the following examples.

EXAMPLE I

This example refers to the preparation, in a standard manner, of tablets A–F for once daily administration. The basic composition of all of the tablets, except for the active substances, is 6.500 mg of corn starch, 1.950 mg of povidone, 0.650 mg of stearic acid, 0.650 mg of colloidal silicone, 0.080 mg of dl-α-tocopherol and 65.000 mg of lactose. The tablets are provided with a coating layer comprising 0.75 mg of hydroxypropylmethylcellulose, 0.15 mg of polyethylene glycol 400, 0.1125 mg of titanium dioxide and 0.1875 of talc.

The tablets all constitute combined means for the administration of a progestogen and an anti-progestogen. The amounts of the active substances are as follows (in mg):

|  | Tablet A | Tablet B | Tablet C | Tablet D | Tablet E | Tablet F |
| --- | --- | --- | --- | --- | --- | --- |
| desogestrel | 0.075 | 0.075 | 0.075 | 0.075 | 0.075 | 0.075 |
| Org 31710 | — | 0.5 | 1.0 | 1.5 | 2.0 | 5.0 |

The only ovulation-inhibiting substance in each tablet is desogestrel.

EXAMPLE II

This Example refers to tablets G–L for once daily administration having the same basic composition and coating layer as in Example I, the amounts of the active substances (in mg) being as follows:

|  | Tablet G | Tablet H | Tablet I | Tablet J | Tablet K | Tablet L |
| --- | --- | --- | --- | --- | --- | --- |
| Org 30659 | 0.075 | 0.075 | 0.075 | 0.075 | 0.075 | 0.075 |
| Org 31710 | — | 0.5 | 1.0 | 1.5 | 2.0 | 5.0 |

The only ovulation-inhibiting substance in each tablet is Org 30659.

EXAMPLE III

This Example refers to a double-blind, placebo controlled, randomised, single centre clinical study in which tablets corresponding to A, C, E, and F are administered to 40 healthy female volunteers in order to investigate an anti-progestogen at three different dosages in the continuous combined regimen according to the invention. Subjects are studied for a period of 180 days, drug intake starting on the first day of a spontaneous menses. One group of 10 women receives tablets A only (in combination with placebo) to serve as a control group. Three groups of 10 women each receive tablets A daily and a dose of Org 31710 every other day, the latter doses differing per group, by being 1 mg, 2 mg, and 5 mg respectively. Recorded daily is, inter alia, bleeding (or absence of bleeding).

EXAMPLE IV

This example refers to an ovulation inhibition test with a combined progestogen and antiprogestogen treatment in stumptailed monkey (Macaca Arctoides).

Experimental design. This test is used to evaluate a combination of a progestogen (desogestrel) and an anti-progestogen (Org 33628) for ovulation-inhibiting activity and effects on cycle-control following daily oral administration for 21 days. Mature female monkeys, *Macaca Arctoides*, with at least 2 regular ovulatory estrous cycles (5–20 year of age, 5–17 kg) are treated from cycle day 2–22. Cycle length is monitored by taking daily vaginal swabs with a cotton tipped applicator. The first day of menstrual bleeding is considered to be day 1 of the cycle and the experiment starts with the pre-treatment control cycle. Blood samples are taken twice a week during the treatment cycle and control cycles (pre-treatment and post-treatment) for determination of estradiol and progesterone which is used to evaluate occurrence of ovulation.

Compound doses. Compounds are administered orally; desogestrel is administered in a dose of 4 μg/kg/day, and the antiprogestin Org 33628 at 0.5 mg/kg/day or 0.1 mg/kg/day.

Evaluation of results: The absence of a luteal progesterone peak (levels above 1 ng/ml) during treatment is considered to be predictable for ovulation inhibition. The absence of a estradiol level above 150 pg/ml during treatment is considered to be an indication of inhibited folliculogenesis.

What is claimed is:

1. A method of treating intermenstrual bleeding in a female, the bleeding induced by administration to the female of a progestogen-only contraceptive regimen on a continuous daily basis, wherein the improvement comprises:

co-administering, on the continuous daily basis for at least 28 consecutive days with the progestogen, an anti-progestogen at a daily dose equivalent, in anti-progestational activity, to a dose of (11β,17β)-11-[4-(dimethylamino)-phenyl]-17-hydroxy-17-(1-propynyl) estra-4,9-diene-3-one of from 0.05 mg to 5 mg to reduce bleeding in the female.

2. The method according to clam 1, wherein the daily dose of anti-progestogen is equivalent, in anti-progestational activity, to a dose of (11β,17β)-11-[4-(dimethylamino)-phenyl]-17-hydroxy-17-(1-propynyl)estra-4,9-diene-3-one of from 0.1 to 2 mg.

3. A method of contraception that inhibits ovulation in a female without increasing the frequency of intermenstrual bleeding, said method comprising:

simultaneously administering to a female, every day for a period of at least 28 days, without a progestogen and anti-progestogen free day:

progestogen in a daily dosage amount sufficient to inhibit ovulation in the female, and anti-progestogen in a daily dosage amount corresponding in anti-progestational activity to from 0.05 mg to 5 mg of (11β,17β)-11-[4-(dimethylamino)-phenyl]-17-hydroxy-17-(1-propynyl)estra-4,9-diene-3-one thus inhibiting ovulation in the female without increasing the frequency of intermenstrual bleeding.

4. The method according to claim 3, wherein the daily dose of anti-progestogen is equivalent to a dose of (11β, 17β)-11-[4-(dimethylamino)-phenyl]-17-hydroxy-17-(1-propynyl)estra-4,9-diene-3-one of from 0,1 to 2 mg.

5. The method according to claim 3, wherein the progestogen is desogestrel, gestodene, or (17α)-17-hydroxy-11-methylene-19-norpregna-4,15-dien-20yh-3-one and the anti-progestogen is (11β,17β)-11-[4-(dimethylamino)-phenyl]-17-hydroxy-17-(1-propynyl)estra-4,9-diene-3-one, (6α,11β,17β)-11-(4-dimethylaminophenyl)-6-methyl-4',5'-dihyrospiro-[estra-4,9-diene-17,2'-(3'H)-furan]-3-one or (11β,17α)-11-(4-acetylphenyl)-17,23-epoxy-19,24-dinorchola-4,9,20-trien-3-one.

* * * * *

UNITED STATES PATENT AND TRADEMARK OFFICE
CERTIFICATE OF CORRECTION

PATENT NO.   : 6,642,219 B1
DATED        : November 4, 2003
INVENTOR(S)  : Herman Jan Tijmen Coelingh Bennink It is certified that error appears in the above-identified patent and that said Letters Patent is hereby corrected as shown below:

Title page,
Item [22], PCT Filed, change "11" to -- 10 --
Item [30], Foreign Application Priority Data, change "98201464" to -- 98201464.9 --
Item [56], References Cited, OTHER PUBLICATIONS, "Wagner H.L., et al., reference, change "REsulting" to -- Resulting --; and change "CervicalRipening" to -- Cervical Ripening --

Column 4,
Line 66, change "better" to -- more --

Column 5,
Lines 13 and 21, after "the" delete "said"

Signed and Sealed this

Fourteenth Day of December, 2004

JON W. DUDAS
*Director of the United States Patent and Trademark Office*